(12) United States Patent
Abrams

(10) Patent No.: US 6,211,426 B1
(45) Date of Patent: Apr. 3, 2001

(54) DEVICES AND METHODS OF TREATMENT FOR PRESSURE ULCERS AND RELATED IMPAIRED BLOOD CIRCULATION PROBLEMS

(76) Inventor: Leonard S. Abrams, 20427 Valley Forge Cir., King of Prussia, PA (US) 19406

( * ) Notice: Subject to any disclaimer, the term of this patent is extended or adjusted under 35 U.S.C. 154(b) by 0 days.

(21) Appl. No.: 09/295,528

(22) Filed: Apr. 21, 1999

Related U.S. Application Data
(60) Provisional application No. 60/112,425, filed on Dec. 16, 1998.

(51) Int. Cl.$^7$ .................................................. A61F 13/00
(52) U.S. Cl. ................................. 602/46; 602/54; 602/60; 602/61; 128/888; 128/889
(58) Field of Search ..................................... 128/888, 889, 128/891, 892, 893, 894; 602/41–59; D24/189

(56) References Cited

U.S. PATENT DOCUMENTS

| | | |
|---|---|---|
| Re. 33,090 | 10/1989 | Berguer . |
| 2,560,712 | 7/1951 | Bell . |
| 2,649,088 * | 8/1953 | Sigg ........................................ 602/48 |
| 3,556,096 | 1/1971 | Fuller et al. . |
| 3,721,232 | 3/1973 | Trenchard . |
| 4,341,209 | 7/1982 | Schaar . |
| 4,655,210 | 4/1987 | Edenbaum et al. . |
| 4,669,460 | 6/1987 | Silber . |
| 4,733,659 | 3/1988 | Edenbaum et al. . |
| 4,972,829 | 11/1990 | Knerr . |
| 5,180,360 * | 1/1993 | Rhame, Jr. .............................. 602/74 |
| 5,356,372 | 10/1994 | Donovan et al. . |

* cited by examiner

Primary Examiner—Kim M Lewis
(74) Attorney, Agent, or Firm—Akin, Gump, Strauss, Hauer & Feld, L.L.P.

(57) ABSTRACT

Bandages for application to the skin of an individual to treat pressure ulcers and other impaired blood circulation problems include a flexible strip having a pair of opposing major planar sides; an adhesive on one of the major sides; and a flexible foam inner member on the one major side of the strip. The foam inner member has a pair of opposing major sides, one being fixed to the strip. At least some of the adhesive on the strip is exposable around the foam member to secure the bandage to an individual. The foam inner member has an outer perimeter extending around and between the major sides of the foam inner member lacking any step extending transversely to the foam inner member and flexible strip sufficiently abruptly to create a discontinuous pressure change along the skin of the individual receiving the bandage and hindering blood flow under the foam inner member. More particularly, the foam members are tapered or undercut to smoothly transition between its two major sides. A foam slipper or boot may be applied over such bandage where the bandage is applied to the foot area or lower leg.

7 Claims, 5 Drawing Sheets

DEVICES AND METHODS OF TREATMENT FOR PRESSURE ULCERS AND RELATED IMPAIRED BLOOD CIRCULATION PROBLEMS

This application claims benefit of Provisional application Ser. No. 60/112,425, filed Dec. 16, 1998.

BACKGROUND OF THE INVENTION

Ulcers can form on the human body where it is subject to long-term, continuous pressure. Such ulcers often arise in bedridden patients whose position is not changed sufficiently frequently. Such ulcers can also form or form more readily in elderly individuals or in those suffering from diabetes or other circulatory problems. Once such ulcers arise, they often become very difficult to treat because of the underlying circulatory problems of the individual.

BRIEF SUMMARY OF THE INVENTION

In one aspect, the invention is a flexible foam material and adhesive material bandage wherein the foam material of the bandage has an outer periphery and lacks any abrupt step at the outer periphery sufficient to develop a pressure ridge against the skin of an individual receiving the bandage.

In another aspect, the invention is a bandage for application to the skin of an individual to treat pressure ulcers and other impaired blood circulation problems comprising: a flexible strip having a pair of opposing major planar sides; an adhesive on one of the pair of major sides of the strip; and a flexible foam inner member on the one major side of the strip, the foam inner member having a pair of opposing major sides, one proximal major side of the foam inner member being fixed to the strip and a remaining distal major side facing away from the strip, at least some of the adhesive on the strip being left uncovered around the foam inner member to secure the bandage to an individual, the foam inner member having an outer perimeter extending entirely around and between the major sides of the foam inner member, the foam inner member diminishing in thickness in the outer perimeter all around the outer perimeter sufficiently smoothly to avoid creation of an abrupt pressure change along the skin of the individual receiving the bandage sufficient to hinder-blood flow through the skin under the foam inner member.

In yet another aspect, the invention is an improved method of treating circulatory problems in an individual comprising the step of applying the aforesaid bandage to the skin of an individual over an area damaged by poor circulation at a pressure therapeutically effective to increase the level of blood circulation through the area beneath the bandage.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings, which are diagrammatic.

DETAILED DESCRIPTION OF THE INVENTION

Figure 1:
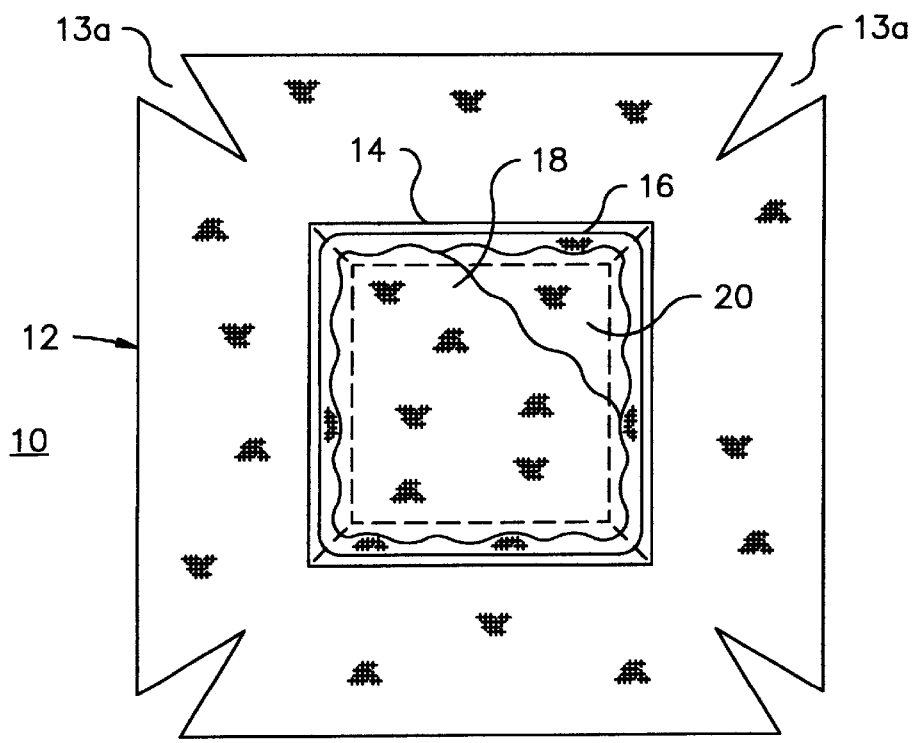
FIG. 1 is a plan view of a first bandage according to the present invention.
Figure 2:
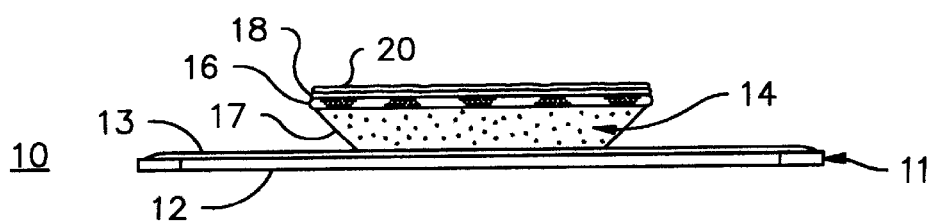
FIG. 2 is a side elevation of the bandage of FIG. 1.

In the drawings, like numerals are used to indicate like elements throughout. FIGS. 1 and 2 depict a first exemplary bandage embodiment according to the present invention indicated generally at 10. The bandage 10 includes an outer, flexible adhesive member 11 in the form of a flexible strip 12 with a layer of adhesive indicated generally at 13 on what is its inner major planar side. The outer major planar side of the strip 12 forms the outer side of the bandage 10. The bandage 10 further includes a flexible foam inner member 14 preferably at least generally planar and generally centered on the strip 12. The adhesive on the inner major side of the strip is preferably used to fix one major side, a proximal side of the inner member 14 facing the strip 12, to the strip 12 and at least some of the adhesive 13 is exposed or exposable under a release strip (not depicted) on the flexible strip 12 extending around the foam inner member 14 to secure the bandage 10 to an individual. Suggestedly, a thin liner 16 formed by a layer of conventional bandage gauze or like material conventionally used to directly contact an open wound is provided on the remaining, distal major side of the foam member 14 facing away from the flexible strip 12, to prevent direct contact of the foam with the user's skin or wound.

Preferably, the adhesive member 11 with adhesive layer 13 is provided by a conventional, non-allergenic, porus adhesive cloth or self-adhesive fabric such as, for example, a Minnesota Mining and Manufacturing Scotch Brand Tape, product code 3M-4, series 2-0300, with a layer 13 of adhesive on one side. A comparable product called "Mefix" is made by Molnlycke Health Care AB of Sweden and distributed in the United States by Scott Health Care. For reasons which will subsequently become apparent, the adhesive member 12 should be as thin as possible. Cutouts 13a may be provided, if desired, to help the bandage 10 conform to the user without wrinkles.

The foam is a flexible, preferably polymer based foam of a density selected to respond to arterial and/or veinal circulatory system pulses in that such pulses deform the foam which springs back to its original position after the arterial or veinal blood vessel begins to relax so that the foam acts like an auxiliary, external blood pump. The foam member is preferably open celled for air passage therethrough. One such recommended foam is a polyether foam grade:

35000XXX, which can be obtained in planar sheet form from the General Foam Corporation, Paramus, N.J. This foam has the following reported characteristics with the applicable ANSI/ASTM-D-3574-95 and GFC Test numbers listed in parentheses: an apparent density of between about 0.77 and 0.97 lbs./ft.$^{3}$; (Test A, GFC Test #1) an indentation force deflection of about 28–34 lbs (using a 50 sq.in. Instron circle) to achieve a 25% deflection in a four (4) inch thick piece of foam, fourteen (14) inches square in size (Test B, GFC Test #2); a tensile strength of about 10 PSI (KPA) (minimum) (Test E, GFC Test #10); an ultimate elongation of 100% (minimum)(Test E, GFC Test #9); , a tear strength of about 1 lb. per inch (minimum) (Test F, GFC Test #8); and a compression set of about 10% loss (maximum) when compressed 90% for about 22 hours at 70° C. (Test D, GFC Test #12). It is believed that similar foams in a range of densities of at least between 0.5 and 6 lbs./ft.$^{3}$ can be used successfully with the present invention.

Preferably, the foam member is about one-half to about one and one-half inches thick. The thinner material is suggested for grade 1 dermatological conditions (redness) while a thicker material is suggested for all dermatological conditions above grade 1. While foams thicker than about one and one-half inch might be used, they can be expected to perform no better than one and one-half inch thick foams. Also it is envisioned that forms of foam other than sheet and conceivably other porous or otherwise gas filled flexible solid materials might be used in place of conventional sheet foam described above.

The liner 16 may be any conventional cotton, polymer or cotton/polymer blend bandage gauze from any of a variety of suppliers. The liner 16 should be as thin as possible for reasons which will become apparent. The gauze may be treated with a Teflon® coating or may be of a Teflon® material to prevent sticking to the wound. For other materials, a coating 18 can be provided on the gauze member 16 of A+D Ointment or other suitable, dermatological ointment. A layer 20 of medication, e.g., an antibiotic and/or antifungal powder or ointment can be applied on the exposed upper surface over or in place of the dermatological ointment for direct contact with the afflicted area.

Suggestedly, the liner 16 and underlying foam member 14 are of a size to fully span and extend beyond the edges of any afflicted area (e.g. any ulcer) and the adhesive member 12 desirably should extend at least two more inches beyond the outer periphery of the foam member 14 (or foam member 14 with gauze 16) on all sides.

Figure 3:
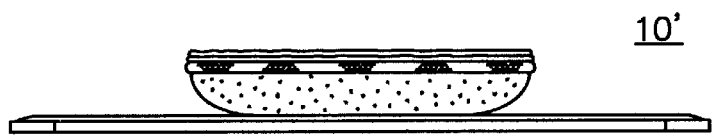
FIG. 3 is a side elevation of a second bandage embodiment having a second, different edge profile.
Figure 4:
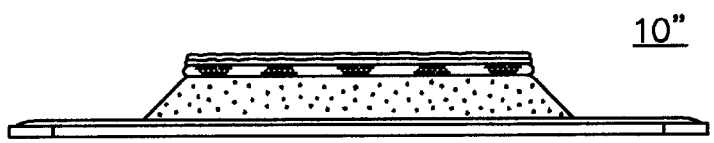
FIG. 4 is a side elevation of a third bandage embodiment having yet a third, different edge profile.

Another important aspect of the invention is illustrated in FIG. 2. It has been found that it is very important to eliminate any sharply delineated edges or other potential pressure sources on the bandages 10. To that end, the thinnest liner 16 is used to minimize any step around the outer perimeter of the liner 16. Also, the suggested foam material, which is supplied in generally planar sheets, is provided with side edges 17 which extend transversely to the major sides of the foam inner member 14 and flexible strip 11 and which are other than perpendicular to the generally planar and parallel opposing major sides of the foam member 14. More specifically, each foam member 14 has an outer perimeter formed by the side edges 17, which extends around and between its pair of opposing major sides. The foam inner member diminishes in thickness in the outer perimeter all around the foam inner member sufficiently smoothly to avoid creation of any abrupt pressure change along the skin of the individual wearing the bandage sufficient to hinder blood flow through the skin under the foam inner member. Thus the perimeter should lack any discontinuity (e.g. transversely extending step or other change in height of the member or the like along the periphery) sufficiently abrupt to create a discontinuous pressure change along the skin of the individual receiving the bandage along the periphery of the foam inner member. Generally speaking, a discontinuity is caused by a sharp edge, that is, a side edge with a surface perpendicular or at least sufficiently near perpendicular to the plane of the foam member 14 to cause the skin at the perimeter of the foam inner member to fold around the edge of the perimeter sufficiently severely to reduce or stop the flow of blood through the fold of the skin.. FIG. 2 illustrates a straight bevel undercut. The depicted flexible foam member 14 is thus inverted frusto-pyramidal. FIG. 3 illustrates a bandage 10' with a foam inner member having a second possible undercut edge profile, which is curvilinear rather than straight. FIG. 4 illustrates a bandage 10' with a foam inner member having a bevel or straight edge treatment, which is tapered rather than undercut. Not illustrated but equally possible is a similarly tapering edge surface which is curvilinear rather than straight. It should be appreciated that undercuts such as those of FIGS. 2 and 3 provides at least as uniform a pressure application as the tapered cut of FIG. 4 while providing more uniform contact of the foam to the wearer's skin over the entire area of the foam and, as such, are preferred. Unless such edge treatment is provided to the foam, or some other treatment is provided to equivalently eliminate any abrupt transition along the outer periphery of the foam member 14, a discontinuous pressure change will be created near the afflicted area which would interfere with blood flow through and immediately below the skin to the afflicted area. To the same end, the adhesive member 11 is also desirably as thin as possible to eliminate the creation of a relatively sharp edge at the outer periphery of either member which can also act as a pressure source cutting off the skin blood flows, especially where the bandaged area of the wearer must be placed upon a support surface.

The bandage 10 is applied to the afflicted area with or without medication on its exposed treatment surface and adhered to the body of the patient for a period of time depending upon a treatment selected. Bandages of the present invention should be applied to the afflicted area with moderate pressure, something between what would be regarded as a loose fitting and a tight fitting for a bandage. The bandage must be applied to the afflicted area with enough pressure so that circulatory system pulses are transmitted to the foam and the foam is able to compress and relax in response to the circulatory system pulses but not so tight as to curtail or diminish the occurrence or strength of the circulatory pulses. Obviously, the optimal pressure will vary for each case. However, some improved coloration or other sign of improved circulation in the afflicted area bandage should be visible within at least 72 hours. These bandages have been successfully left in place for up to three days. The bandage should be removed after three days and the afflicted area cleaned and treated and a new bandage applied, if necessary. This is a shorter time with less pain, minimal surgery and minimal scar tissue.

Figure 5:
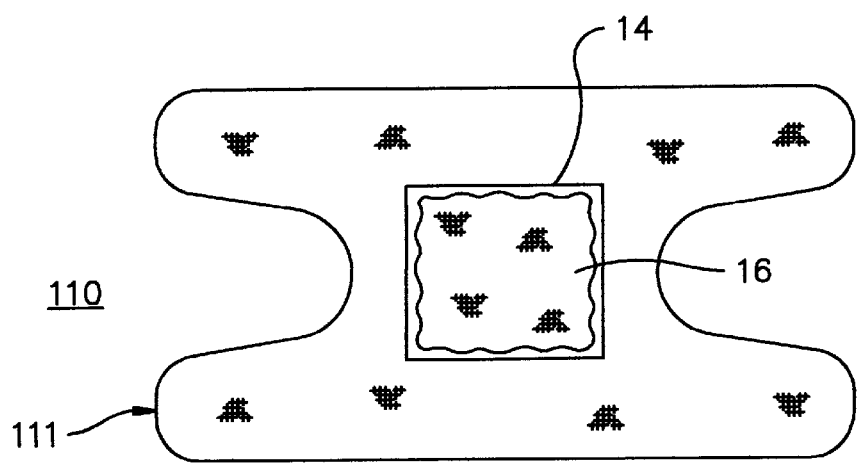
FIG. 5 is a top plan view of a fourth bandage embodiment different in size from the earlier embodiments.

Bandages of the present invention can be provided in various sizes and/or the proportions of the adhesive member 11 varied with respect to the flexible foam member 14 and/or liner 16, as indicated by the bandage embodiment 110 shown in FIG. 5. Bandage 100 illustrates another form of cut-outs (i.e., butterfly). It is expected that the present invention can be adapted to be used with virtually any conventional or special form of adhesive bandage.

While generally square/rectangular bandages and components are shown, these are intended to only be illustrative. Their use is based, in large part, upon the widespread availability of rectangularly shaped bandages and bandage components and requirements of the present invention.

The outlines of the foam member 14 and liner 16 can be defined by straight lengths as shown for a rectangular or polylateral shape or fully curvilinear (not shown) or a combination of straight and curvilinear lengths (also not shown). Indeed, if the components 11, 14 and/or 16 are especially made, it may be desirable to make them in curvilinear or combination curvilinear/linear shapes to reduce the likelihood of creating any corners or sharp edges which could constitute a potential source of pressure discontinuity on the bandage itself.

Adhesive bandages 10, 110 and the like described above can be used on virtually any exposed surface of the human body which may become ulcerated from pressure (i.e., bed sores). Ulceration can also occur simply from poor blood circulation. Limbs are most affected.

Figure 6:
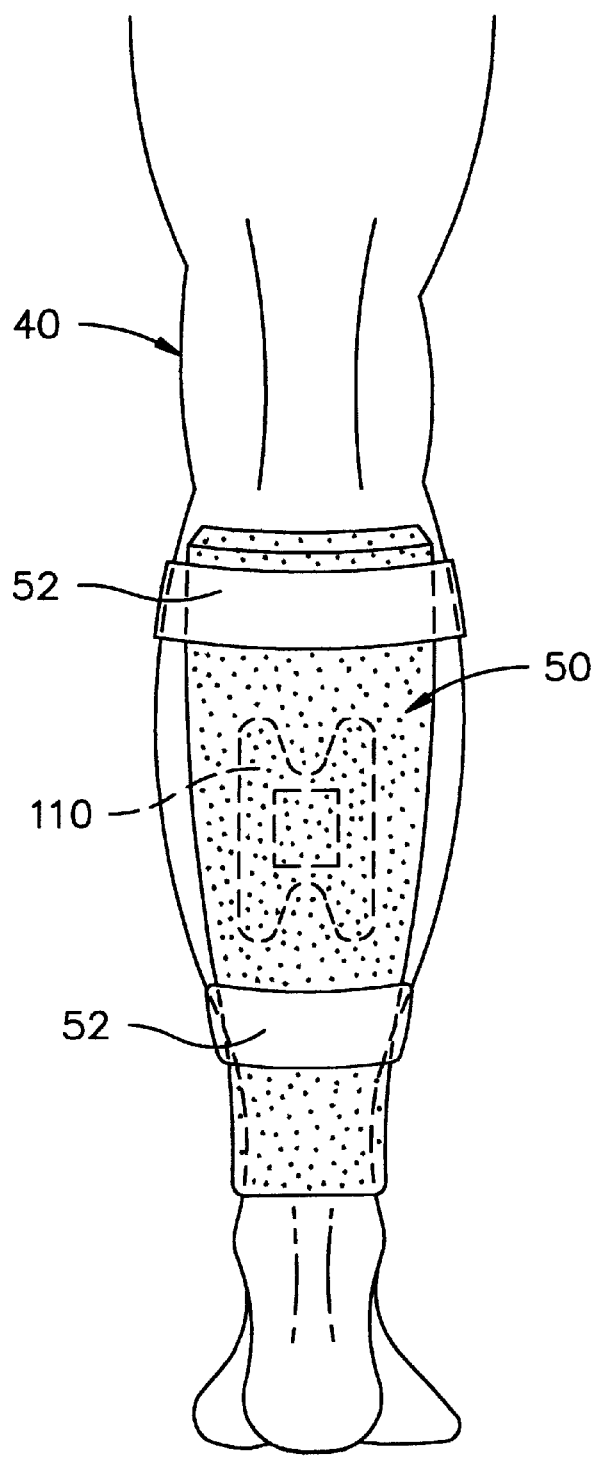
FIG. 6 is a illustrates one of the bandages of the previous figures being used on a patient's limb with an auxiliary foam pad.

FIG. 6 illustrates schematically, the use of one of the bandages (110) of the present invention on a limb, for example, a leg 40, to increase the flow of blood into the afflicted area from beyond the bandage 10 itself. A separate strip or patch 50 of the aforesaid flexible foam material is applied over the bandage 10 or 110, overlapping the bandage and extending beyond the bandage, preferably in a longitudinal orientation with respect to the limb, to improve circulation back and forth along the limb through of the afflicted area. The strip or patch 50 may be held in position against the limb 40 by one or more strips 52 of adhesive material, preferably the same adhesive cloth material mentioned above for use as the adhesive member 11. The strip/patch 50 defines a corridor along which the flow of blood is assisted or boosted. Suggestedly, a length of elastic fabric tubing of the type commonly used on limbs before casts are applied is applied over the affected limb and over the strip/patch 50 to hold substantially if not essentially all of the patch/strip 50 against the limb 40 to provide greater foam/skin contact for more efficient auxiliary pumping action by the strip/patch 50. FIG. 6 illustrates use of the foam strip/patch 50 to improve circulation in the calf and below. Suggestedly, the strip/patch 50 extends from just above the tendo-Achilles insertion of the tendon to the top of the calf muscle just below the knee. While two adhesive strips 52 are shown, more could be used. Alternatively, the foam patch/strip 50 could be held in place with a cloth wrap or a length of elastic fabric tubing or a stocking.

Figure 7:
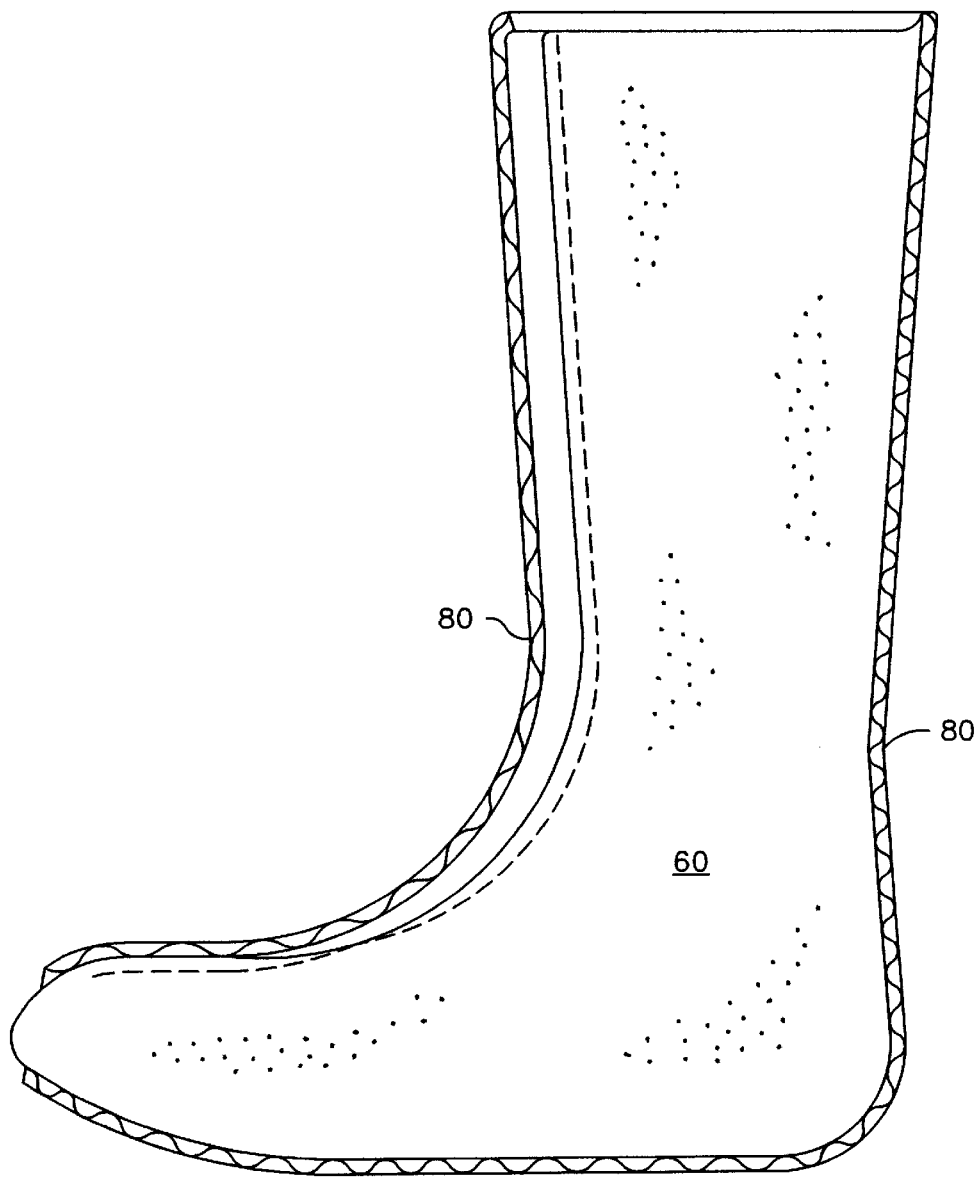
FIG. 7 is a side elevation of an auxiliary foam boot which may be used with or without a bandage of the present invention.
Figure 8:
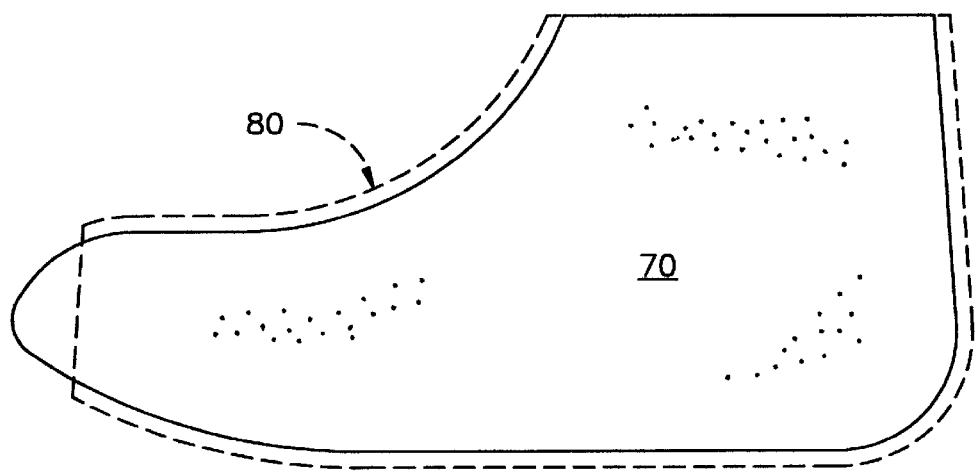
FIG. 8 is a side elevation of an auxiliary foam low boot, which may be used with or without bandages of the present invention.
Figure 9:
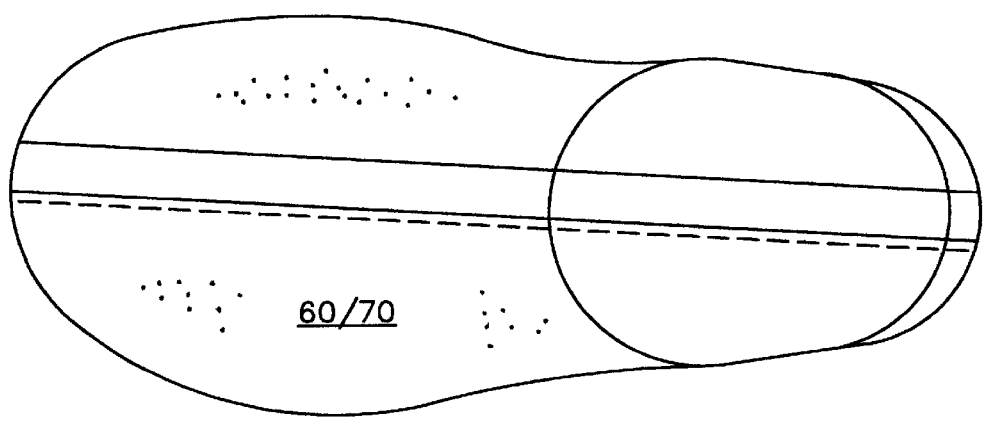
FIG. 9 is a top plan view of the boots of FIGS. 7 and 8.

Feet and/or lower legs are typically the extremities initially or most seriously affected by poor blood circulation. To that end, FIGS. 7–9 depict an exemplary high foam boot 60 and a low foam boot 70, respectively, which would be used in place of a conventional length of foam-like strip/patch 50 on the foot or foot and lower leg area. Either boot 60 or 70 may be formed from the aforesaid foam material, preferably one and one-half inch thick foam material, and applied over the user's foot and over any bandage of the present invention like 10 or 110, which is applied directly to an affected area. Either boot may be held in place in close contact with the skin of the foot or foot and lower leg by suitable means such as an elastic bandage or a length of the elastic fabric tubing 80 of the type referred to above. Such boots 60,70 may be made manually by simply wrapping a length of flexible foam sheet around the foot or foot and lower leg and cutting away the overlapping portion of the foam to leave a single, foam layer covering, which can be held in place by elastic bandage or elastic fabric tubing. It is also envisioned that such boots can be specially made, suggestedly in various sizes (e.g., small, medium, long and extra long), and provided with such amenities as Velcro® closures for long term durability and ease of use. Preferably, the high boot extends upward to the tuberosity of the tibia at the knee joint. It is also envisioned that such boots might be made with a foam having its own elastic character or may be formed with an elasticized material so that it may be slipped on and off and worn like a slipper-sock. The boots 60,70 can be used without underlying bandages to encourage foot or foot and lower leg blood circulation even before circulatory injuries arise.

While various embodiments of the invention have been disclosed, other embodiments of different shapes and sizes and substitute other known material or materials which may be developed at a future time as the described materials to perform the same function are considered to part of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A bandage for application to the skin of an individual to treat pressure ulcers and other impaired blood circulation problems comprising:

a flexible strip having a pair of opposing major planar sides;

an adhesive on one of the pair of major sides; and a flexible foam inner member on the one major side of the strip, the foam inner member having a pair of opposing major sides, one major side of the foam inner member being fixed to the strip and a remaining major side facing away from the strip, and a plurality of side edges connecting the major sides, at least some of the adhesive on the strip being left uncovered around the foam inner member to secure the bandage to an individual, the foam inner member having an outer perimeter defined by the side edges extending around and between the major sides of the foam inner member, the side edges tapering from one major side to the other such that the foam inner member diminishes in thickness in the outer perimeter all around the outer perimeter sufficiently smoothly to avoid creation of an abrupt pressure change along the skin of the individual receiving the bandage sufficient to hinder blood flow through the skin under the foam inner member;

wherein the flexible foam inner member is effective therapeutically to respond to underlying circulatory system pulses and provide arterial or veinal auxiliary pumping action to the skin surface underlying the flexible foam material.

2. The bandage of according to claim 1 in further combination with an overlying flexible foam member effective therapeutically to provide arterial or venial auxiliary pumping action to the skin surface contacted by the overlying foam member around the skin area covered by the bandage.

3. The bandage of according to claim 1 further comprising a thin liner over the foam inner member to prevent direct contact of a wearer's skin with the foam inner member.

4. The bandage of claim 1 in combination with footwear formed of a flexible foam material responsive to arterial or venial pulses in a lower limb extremity and therapeutically effective to increase blood circulation to the lower limb by acting as a passive, auxiliary external pump.

5. The combination of claim 4 in further combination with an outer elastic member holding the inner surface of the footwear in operative contact with any foot in the footwear.

6. An improved method of treating circulatory problems in an individual comprising the step of applying the bandage and footwear of claim 5 to the lower limb of an individual over an area damaged by poor circulation at a pressure therapeutically effective to increase the level of blood circulation through the area beneath the bandage and within the footwear.

7. An improved method of treating circulatory problems in an individual comprising the step of applying the bandage of claim 1 to the skin of an individual over an area damaged by poor circulation at a pressure therapeutical effective to increase the level of blood circulation through the area beneath the bandage.

* * * * *